United States Patent [19]

Satek et al.

[11] Patent Number: 4,766,102

[45] Date of Patent: Aug. 23, 1988

[54] SILVER ALUMINUM BORATE OXIDATION CATALYST AND PROCESS FOR ITS PREPARATION

[75] Inventors: Larry Satek, Wheaton, Ill.; Laura Wilwerding, Earling, Iowa; John L. Melquist, Naperville; Melvin L. Luetkens, Lisle, both of Ill.

[73] Assignee: Amoco Corporation, Chicago, Ill.

[21] Appl. No.: 17,315

[22] Filed: Feb. 20, 1987

[51] Int. Cl.$^4$ .................... B01J 21/02; B01J 21/04; B01J 23/50

[52] U.S. Cl. .................... 502/202; 423/600; 558/321

[58] Field of Search .................... 502/202; 423/600; 558/321

[56] References Cited

U.S. PATENT DOCUMENTS 3,856,702 12/1974 McArthur .................... 502/202 X
3,933,686 1/1976 Ferlazzo et al. .................... 502/317

Primary Examiner—W. J. Shine
Attorney, Agent, or Firm—Matthew R. Hooper; William H. Magidson; Ralph C. Medhurst

[57] ABSTRACT

The present invention relates to a novel silver aluminum borate composition useful as a catalyst for oxidation and/or ammoxidation reactions. More particularly the invention is directed to silver aluminum borate having the general formula (x) $Ag_2O \cdot$(y) $Al_2O_3 \cdot$(z) $B_2O_3$ where x, y and z are numbers representing molar amounts of the oxides such that the mole fraction of $Ag_2O$, calculated as $x/(x+y+z)$ is from about 0.35 to about 0.60, the mole fraction of $Al_2O_3$, calculated as $y/(x+y+z)$ is from about 0.10 to about 0.40, and the mole fraction of $B_2O_3$, calculated as $z/(x+y+z)$ is from about 0.10 to about 0.45. The invention is further directed to a method for preparing the catalyst, and to its use as an oxidation or ammoxidation catalyst.

11 Claims, No Drawings

SILVER ALUMINUM BORATE OXIDATION CATALYST AND PROCESS FOR ITS PREPARATION

The present invention relates to a novel silver aluminum borate composition useful as a catalyst for oxidation and/or ammoxidation reactions. More particularly the invention is directed to silver aluminum borate having the general formula (x) $Ag_2O \cdot$ (y) $Al_2O_3 \cdot$ (z) $B_2O_3$ where x, y and z are numbers representing molar amounts of the oxides such that the mole fraction of $Ag_2O$, calculated as $x/(x+y+z)$ is from about 0.35 to about 0.60, the mole fraction of $Al_2O_3$, calculated as $y/(x+y+z)$ is from about 0.10 to about 0.40, and the mole fraction of $B_2O_3$, calculated as $z/(x+y+z)$ is from about 0.10 to about 0.45. The invention is further directed to a method for preparing the catalyst, and to its use as an oxidation or ammoxidation catalyst.

The use of silver or supported silver as a mild oxidation catalyst is known in the art. Solomon U.S. Pat. No. 4,255,341 discloses a supported silver containing catalyst suitable for the oxidation of ethylene to ethylene oxide. Solomon states the most commonly used technique of preparing a supported silver oxidation catalyst has involved: preparing silver oxide by treating an aqueous solution of silver nitrate with an alkali metal hydroxide; recovering the silver oxide; depositing the silver oxide on the support; and activating the catalyst by reduction or calcination. Solomon discloses a simplified method wherein aqueous silver nitrate is combined with a suitable solid support followed by drying and calcining steps. An especially preferred support is alpha alumina. Solomon neither discloses nor suggests a mixed oxide composition of silver aluminum and boron.

Ammoxidation is a well-known reaction for the formation of carbon nitrogen bonds. For example the reaction is used to convert propylene to acrylonitrile, toluene to benzonitrile, and xylenes to phthalonitriles. The technical literature indicates that many of the ammoxidation catalysts used for aromatic substrates contain vanadium as the active ingredient. Angstadt U.S. Pat. No. 4,070,393 discloses a vanadium bronze ammoxidation catalyst which can comprise copper, silver, tin, uranium and thorium, etc.

We have now discovered a new crystalline composition, silver aluminum borate, which exhibits activity as an oxidation and/or ammoxidation catalyst. In particular the present invention in its composition aspect is directed to silver aluminum borate having the general formula (x) $Ag_2O \cdot$ (y) $Al_2O_3 \cdot$ (z) $B_2O_3$ where x, y and z are numbers representing the relative molar amounts of the oxides such that the mole fraction of $Ag_2O$, calculated as $x/(x+y+z)$ is from about 0.35 to about 0.60, the mole fraction of $Al_2O_3$, calculated as $y/(x+y+z)$ is from about 0.10 to about 0.40, and the mole fraction of $B_2O_3$, calculated as $z/(x+y+z)$ is from about 0.10 to about 0.45.

Silver aluminum borate compositions according to the present invention are characterized by a unique crystalline phase as indicated by X-ray powder diffraction crystallography. We have been unable to attribute the unique X-ray pattern of silver aluminum borate to any known composition. X-ray data were determined by standard techniques. The radiation was the K-alpha double lines of copper on a Scintag PAD IV spectrometer equipped with a liquid nitrogen cooled germanium solid state detector. The peak heights, I and the positions as a function of 2 times theta where theta is the Bragg angle, were read from the spectrometer chart. From these the relative intensities, 100 I/Io, where Io is the intensity of the strongest peak, and d (obs.), the interplanar spacing in A, corresponding to the recorded lines, were calculated.

X-ray data for a representative range of silver aluminum borate compositions prepared according to the present invention are set forth in Table A below. As can be seen from the table, a combination of unidentified lines recur in approximately the same relative intensities in the silver aluminum borate mixed oxide composition of the present invention having a mole fraction of $Ag_2O$ in the range of about 0.35 to about 0.60, a mole fraction of $Al_2O_3$ in the range of about 0.10 to about 0.40, and a mole fraction of $B_2O_3$ in the range of about 0.10 to about 0.45.

TABLE A

| | | | Silver Aluminum Borate X-Ray Analyses | | | | | | | | |
|---|---|---|---|---|---|---|---|---|---|---|---|
| | | Calc. | d (obs.) and Relative Intensities | | | Calc. | d (obs.) and Relative Intensities | | | | | |
| | Ag:Al:B | Temp. °C. | 1.45 | 1.47 | 1.75 | Temp.°C. | 1.85 | 1.93 | 2.10 | 2.43 | 2.85 | 4.22 |
| I. | 2:1:1 | 400 | 42 | 56 | 28 | 400 | 35 | 16 | 63 | 47 | 100 | 37 |
| II. | 9:6:5 | 600 | 60 | 59 | 26 | 600 | 33 | 14 | 52 | 57 | 100 | 45 |
| III. | 4:3:3 | 400 | 33 | 52 | 23 | 400 | 32 | 10 | 38 | 46 | 100 | 38 |
| | | 600 | 43 | 46 | 26 | 600 | 32 | 16 | 36 | 45 | 100 | 29 |
| IV. | 2:1:2 | 400 | — | 48 | 19 | 400 | 32 | — | 52 | 45 | 100 | 32 |
| | | 600 | 31 | 39 | 41 | 600 | 30 | 31 | 54 | 31 | 100 | 19 |
| V. | 8:5:7 | 400 | 46 | 51 | 23 | 400 | 34 | 14 | 46 | 80 | 100 | 37 |
| | | 600 | 34 | 44 | 28 | 600 | 31 | 18 | 52 | 35 | 100 | 27 |
| VI. | 9:4:7 | 400 | 48 | 52 | 22 | 400 | 28 | 17 | 35 | 43 | 100 | 35 |
| | | 600 | 37 | 34 | 27 | 600 | 24 | 23 | 27 | 26 | 100 | 21 |
| VII. | 11:3:6 | 600 | 50 | 34 | 30 | 600 | 26 | 28 | 30 | 30 | 100 | 28 |

Briefly, the silver aluminum borate ammoxidation catalyst of the present invention can be prepared by combining reagents comprising suitable precursors of silver oxide ($Ag_2O$), aluminum oxide ($Al_2O_3$) and boron oxide ($B_2O_3$) and calcining the combined reagents. Preferably the reagents are mixed in a liquid medium, following which the liquid is removed and the combination is calcined.

Suitable precursors of silver oxide include any boron salt containing a decomposable anion such as silver nitrate, silver acetate, silver formate, silver carbonate, etc. Suitable precursors of boron oxide include any boron salt containing a decomposable anion such as boric acid, silver borate, aluminum borate, boron oxides and ammonium borate. Suitable precursors of $Al_2O_3$ include any aluminum salt containing a decomposable anion such as alumina sols, aluminum nitrate, alumina, aluminum acetate, aluminum borate, etc. A high surface reactive alumina source is preferred such as Davison PHF alumina sol. These precursors are combined in relative molar amounts such that the final calcined silver aluminum borate is characterized by the mixed oxide formula (x) $Ag_2O \cdot (y) Al_2O_3 \cdot (z) B_2O_3$ where x, y and z represent the relative molar amounts of the oxides (based on the starting molar amounts of the precursor reagents) and the mole fraction of $Ag_2O$ is from about 0.35 to about 0.60, the mole fraction of $Al_2O_3$ is from about 0.10 to about 0.40, and the mole fraction of $B_2O_3$ is from about 0.10 to about 0.45.

In somewhat greater detail, a typical preferred preparation of the silver aluminum borate ammoxidation catalyst of the present invention can be carried out by preparing an aqueous solution of alumina sol, boric acid, and silver nitrate and mixing in a blender for 3–5 minutes followed by gellation with ammonia. The presence of the ammonia as well as other volatile components in preparation of the silver aluminum borate, such as acetate ion, nitrate ion, etc., is advantageous in providing the final calcined catalyst with sufficiently high surface area and porosity desirable for catalytic reactions. The gelled catalyst precursor is allowed to air dry, usually for about 1–3 days, followed by vacuum drying, typically for about 15 to 25 hours at about 100° C. to 150° C. with a nitrogen purge. Calcination is carried out at between 350° C. and 650° C. The preferred calcination temperature is about 500° C. to 600° C. Above about 650° C., crystallinity is lost and the samples are mostly amorphous with some metallic silver. Temperatures below about 350° C. are insufficient to form the unique crystalline phase having the significant X-ray lines of Table A. Calcination can be carried out in air, nitrogen or other inert gases. Preferably, during calcination it is generally desirable to exclude light to prevent formation of elemental silver. Also a preferred atmosphere for calcination is oxygen as it prevents formation of elemental silver.

In a preferred embodiment of the above-described method, to avoid the undesirable appearance of considerable amounts of elemental silver in the catalyst samples prepared according to the present invention, the dried precursor, prior to calcination, is dissolved in concentrated nitric acid, followed by removal of the remaining liquid by evaporation and/or vacuum drying and final calcination. Most preferably, to eliminate the time required to allow the precursor gel to air-dry before the nitric acid is added, portions of the gel can be poured into a crystallizing dish to which concentrated nitric acid can be added. Water can then be evaporated on a hot plate and the precursor mixture vacuum dried and calcined. We note that unless all of the water is driven off the precalcined material during drying, the precursor remains hygroscopic. However, once completely dry, the precursor samples are stabilized against any further hygroscopic tendency. The cause for this phenomenon is presently unknown.

The above preferred technique for preparing the catalyst which involves addition of nitric acid to the precursor mixture prior to calcination (and most preferably prior to drying) is beneficial in reducing the amount of elemental silver in the final catalyst. This is supported in that we have found, for samples prepared using nitric acid, increasing calcination temperature generally caused an increase in the amount of elemental silver in the calcined catalyst, whereas samples prepared without nitric acid contained elemental silver regardless of calcination temperature, indicating that some of the silver nitrate was most likely reduced to elemental silver during the air drying of the samples prepared without nitric acid. As stated above, the use of an oxygen atmosphere for catalyst preparation is a further measure for reducing the formation of elemental silver in the precursor.

Silver aluminum borate prepared according to the procedures outlined above is an active catalyst for ammoxidation reactions in which a suitable hydrocarbon is converted to the corresponding nitrile by reaction with the catalyst in the presence of $O_2$ and/or ammonia under ammoxidation conditions. In particular the novel catalyst of the present invention can be used for conversion of light olefins, preferably $C_2$ to $C_6$, to unsaturated nitriles, i.e., propylene to acrylonitrile, etc., and for conversion of alkyl substituted aromatics to the corresponding nitriles, i.e., toluene to benzonitrile, xylenes to tolunitriles and phthalonitriles, etc. In addition, silver aluminum borate according to the present invention can be used for oxidation of lower ($C_2$–$C_{10}$) alkenes to their corresponding epoxides, and for oxidation of $C_2$–$C_{10}$) alkenyl aromatics to the corresponding aromatic epoxides. Thus ethylene and propylene can be converted to ethylene oxide and propylene oxide. In addition styrene and p-methylstyrene can be converted to styrene oxide and p-methylstyrene oxide.

EXAMPLE I

A silver aluminum borate having the approximate formula 8 $Ag_2O \cdot 5\ Al_2O_3 \cdot 7\ B_2O_3(Ag_8Al_5B_7O_{22})$ and the significant X-ray lines of Table A was prepared as follows: 27.1g (0.44 moles) of boric acid crystals (Mallinckrodt, reagent grade) were placed in a 250 ml beaker and 150 ml (150 g) of distilled water were added to the beaker. A magnetic stir bar was placed in the beaker and the beaker was placed on a hot plate stirrer at medium settings. The mixture was heated and stirred until all the crystals had dissolved. To prepare a silver nitrate solution, 85.0 g (0.50 moles) of silver nitrate crystals were placed in a 150 ml beaker. Thirty-five milliliters of distilled water were added to the beaker. A magnetic stir bar was placed in the beaker and the beaker was placed on a hot plate stirrer set at low heat and rapid stirring until all the crystals had dissolved. A 7.8 percent alumina sol (PHF alumina) was used. The sol, 204.4 g (15.9 g alumina, 0.16 moles alumina) was weighed into a 250 ml beaker to which the boric acid and silver nitrate solutions were added. The alumina sol, boric acid solution and silver nitrate solution were poured into a blender that had the metal fittings of the blade assembly coated with epoxy. The mixture was blended for 4–5 minutes, alternating between low and high speeds every 30–60 seconds. The sides of the container were occasionally scraped. To the mixture in the blender, 7.5 ml (6.75 g, 0.19 moles) of concentrated $NH_4OH$ were added and the mixture was blended for approximately one minute on low speed. The mixture was spread onto a 36 cm×46 cm plastic tray and covered with foil. The mixture was allowed to air-dry for three days. The sample was scraped into a 170 mm×90 mm glass crystallizing dish. To the mixture, 50 ml (71 g, 1.13 moles) of concentrated $NHO_3$ and 100 ml (100 g) of distilled water were added. The mixture was stirred and left standing for one hour. The mixture was heated on a hot plate for 2–3 hours until the sample was almost completely dry. The sample was vacuum dried at 120° C. and 0.4 atm pressure with a nitrogen purge for 21½ hours. A portion of the mixture was calcined as follows: 120° C. to 165° C. (gradually over about 2 hours); 165° C. to 600° C. (gradually over about 4 hours); 600° C.

(for about 8 hours); 600° C. to 120° C. (gradually over about 3 hours); and 120° C. to 50° C. (over about 1 hour).

EXAMPLE II

The silver aluminum borate catalyst prepared in accordance with Example I was evaluated for the ammoxidation of toluene to benzonitrile at 400° C. to 450° C. at dilute oxygen flow rates, as follows: 1.0 cm$^3$ of 18/35 mesh catalyst was mixed with 0.3 cm$^3$ of 18/35 mesh alpha alumina, an inert diluent. This mixture of solids was supported on a bed of alpha alumina and a glass wool plug in a 6 mm OD×19 cm long vycor reactor tube. The packed tube was heated to reaction temperature (400° C. or 450° C.) by a small electric tube furnace. The oxidant, O$_2$, was supplied to the reactor diluted to about 8 percent with N$_2$. The liquid feeds (i.e., toluene and water) were metered into the reactor by a syringe pump. Ammonia was fed as a gas. The reaction was evaluated at one atmosphere total pressure. The products were maintained in the gaseous state until they had passed through a G.C. sampling valve which allowed periodic analysis of the organic products. Periodic samples of the noncondensable gases were analyzed by G.C. for O$_2$, N$_2$, CO and CO$_2$. The results of this evaluation are given in Table I, below. As can be seen from the data, silver aluminum borate of the present invention is an active ammoxidation catalyst.

TABLE I

| Temp. (°C.) | Dilute O$_2$ Flow Rate ml/sec | NH$_3$ Flow Rate ml/sec | Toluene and H$_2$O Flow Rate | Products (% area by G.C.) | | |
|---|---|---|---|---|---|---|
| | | | | Benzene | Toluene | Benzonitrile |
| 400 | 0.22 | 0.018 | 0.00282 | 12.3 | 79.6 | 7.6 |
| 400 | 0.22 | 0.018 | 0.00282 | 10.8 | 80.3 | 8.7 |
| 400 | 0.22 | 0.018 | 0.00282 | 9.4 | 82.2 | 8.3 |
| 400 | 0.29 | 0.018 | 0.00282 | 11.3 | 78.9 | 9.6 |
| 450 | 0.22 | 0.018 | 0.00282 | 17.0 | 74.8 | 8.1 |

EXAMPLE III

Silver aluminum borate compositions I–IV, VI and VII from Table A were prepared in accordance with the procedures outlined in Example I. These compositions having the unique crystalline structure of silver aluminum borate characterized by the significant X-ray lines of Table A are also catalysts for ammoxidation. Individual compositions can be evaluated for specific hydrocarbon conversions using the procedures of Example II.

What is claimed is:

1. Silver aluminum borate of the general formula (x) Ag$_2$O.(y)Al$_2$O$_3$.(z)B$_2$O$_3$ where x, y and z are numbers representing molar amounts of the oxides such that the mole fraction of Ag$_2$O, calculated as $x/(x+y+z)$ is from about 0.35 to about 0.60, the mole fraction of Al$_2$O$_3$, calculated as $y/(x+y+z)$ is from about 0.10 to about 0.40, and the mole fraction of B$_2$O$_3$, calculated as $z/(x+y+z)$ is from about 0.10 to about 0.45.

2. The silver aluminum borate of claim 1 having the significant X-ray diffraction lines of Table A.

3. The silver aluminum borate of claim 2 having substantially the formula Ag$_8$Al$_5$B$_7$O$_{22}$.

4. A process for preparing silver aluminum borate which comprises: combining suitable precursors of silver oxide (Ag$_2$O), aluminum oxide (Al$_2$O$_3$) and boron oxide (B$_2$O$_3$) in a liquid medium and calcining the combined precursors to produce an active catalyst.

5. The process of claim 4 wherein the relative amounts of the precursors are such that, upon calcination at a sufficiently high temperature, crystalline silver aluminum borate is formed having the significant X-ray diffraction lines of Table A.

6. The process of claim 5 wherein the liquid medium is essentially completely removed prior to calcining.

7. The process of claim 6 wherein the liquid medium contains aqueous ammonia.

8. The process of claim 5 wherein the calcination is carried out at about 350° C. to about 650° C.

9. The process of claim 7 wherein the calcination is carried out at about 500° C. to about 600° C.

10. The process of claim 6 wherein nitric acid is added to the liquid precursor combination.

11. The process of claim 6 further comprising the steps of adding a solution of nitric acid to the essentially liquid-free precursor combination, followed by essentially complete removal of water from the acidified precursor solution prior to calcining.

* * * * *